United States Patent
Yanaizumi et al.

(10) Patent No.: US 9,840,484 B2
(45) Date of Patent: Dec. 12, 2017

(54) ARYL COMPOUND AND MAKING METHOD

(71) Applicant: Shin-Etsu Chemical Co., Ltd., Tokyo (JP)

(72) Inventors: Kazuhide Yanaizumi, Annaka (JP); Hideyoshi Yanagisawa, Annaka (JP)

(73) Assignee: SHIN-ETSU CHEMICAL CO., LTD., Tokyo (JP)

( * ) Notice: Subject to any disclaimer, the term of this patent is extended or adjusted under 35 U.S.C. 154(b) by 0 days.

(21) Appl. No.: 15/398,838

(22) Filed: Jan. 5, 2017

(65) Prior Publication Data

US 2017/0197928 A1 Jul. 13, 2017

(30) Foreign Application Priority Data

Jan. 7, 2016 (JP) .................................. 2016-001905
Dec. 21, 2016 (JP) .................................. 2016-247324

(51) Int. Cl.
 *C07D 303/30* (2006.01)
(52) U.S. Cl.
 CPC ................................. *C07D 303/30* (2013.01)
(58) Field of Classification Search
 CPC .................................................. C07D 303/30
 See application file for complete search history.

(56) References Cited

U.S. PATENT DOCUMENTS

| 6,709,753 B2 | 3/2004 | Honda et al. |
| 2003/0078322 A1 | 4/2003 | Honda et al. |

FOREIGN PATENT DOCUMENTS

| JP | 11-130838 A | 5/1999 |
| JP | 2002-249584 A | 9/2002 |

OTHER PUBLICATIONS

Extended European Search Report dated Mar. 6, 2017, issued in counterpart European Application No. 16207328.2. (6 pages).

*Primary Examiner* — John M Mauro
(74) *Attorney, Agent, or Firm* — Westerman, Hattori, Daniels & Adrian, LLP

(57) ABSTRACT

An aryl compound terminated with at least three glycidyl groups and at least three (meth)allyl groups, having formula (1) wherein $R^1$ is a $C_3$-$C_{20}$ hydrocarbon, $R^2$ is hydrogen or methyl, and n is 3 or 4 is novel. It is prepared by reacting an aryl compound having at least three (meth)allyl-containing phenol groups with a 2-halomethyloxirane.

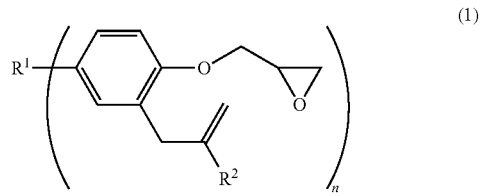

(1)

5 Claims, No Drawings

ARYL COMPOUND AND MAKING METHOD

CROSS-REFERENCE TO RELATED APPLICATION

This non-provisional application claims priority under 35 U.S.C. §119(a) on Patent Application No. 2016-001905 filed in Japan on Jan. 7, 2016, the entire contents of which are hereby incorporated by reference.

TECHNICAL FIELD

This invention relates to a novel aryl compound having at least three glycidyl groups and at least three (meth)allyl groups in the molecule and a method for preparing the same.

BACKGROUND ART

Compounds having glycidyl and (meth)allyl groups are known in the art. For example, Patent Document 1 discloses a compound of the following formula:

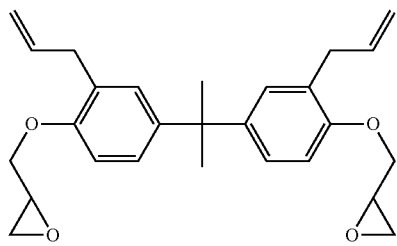 [SMILES: C=CCc1cc(C(C)(C)c2ccc(OCC3CO3)c(CC=C)c2)ccc1OCC1CO1]

which is commercially available under the trade name of RE-810NM from Nippon Kayaku Co., Ltd. Since the compound has two epoxy groups in the monomer molecule, a linear polymer is formed by linking epoxy groups, which exhibits poor heat resistance and loses bond strength when exposed to high temperature.

Patent Document 2 discloses a compound of the following formula.

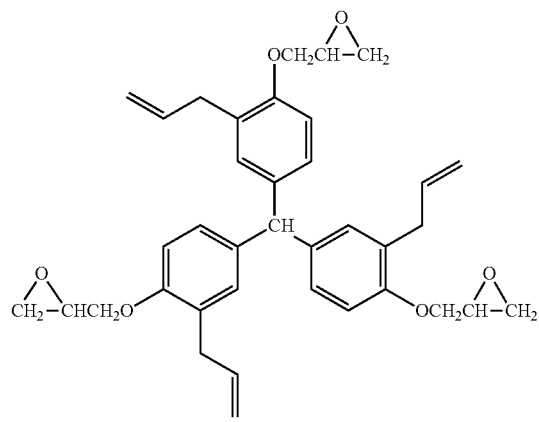

In this compound, three phenyl groups having epoxy and allyl are bonded to methyl. The compound has poor heat resistance because the linking hydrocarbon is a low molecular weight one like methyl. This raises the problem that a polymer of the compound with a siloxane is less resistant to CVD film formation and loses bond strength.

CITATION LIST

Patent Document 1: JP-A H11-130838
Patent Document 2: JP-A 2002-249584 (U.S. Pat. No. 6,709,753)

SUMMARY OF INVENTION

An object of the invention is to provide a novel aryl compound having glycidyl and (meth)allyl groups which overcomes the aforementioned disadvantages and shortcomings and a method for preparing the compound.

The inventors have found that an aryl compound having at least three glycidyl groups and at least three (meth)allyl groups in the molecule, represented by the general formula (1):

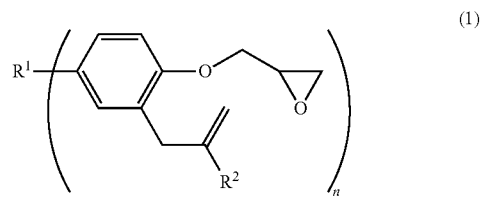

is prepared by reacting an aryl compound having at least three (meth)allyl-containing phenol groups, represented by the general formula (2):

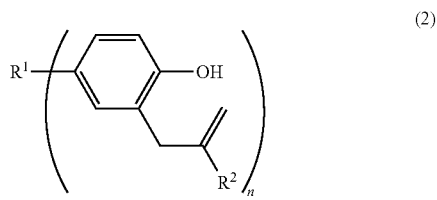

with a 2-halomethyloxirane having the following formula (3):

wherein $R^1$ is a trivalent or tetravalent $C_3$-$C_{20}$ hydrocarbon group, $R^2$ is hydrogen or methyl, n is 3 or 4, and X is halogen, and that a polymer formed using the aryl compound of formula (1) has satisfactory strength, heat resistance, weather resistance, and water resistance.

In one aspect, the invention provides an aryl compound terminated with glycidyl and (meth)allyl groups, having the general formula (1).

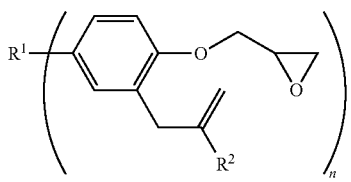

Herein $R^1$ is a tri- or tetravalent $C_3$-$C_{20}$ hydrocarbon group, $R^2$ is hydrogen or methyl, and n is 3 or 4.

Preferably, $R^1$ is a tri- or tetravalent $C_3$-$C_{15}$ hydrocarbon group, more preferably having at least an aromatic or alicyclic group. Most preferably, $R^1$ is selected from the following.

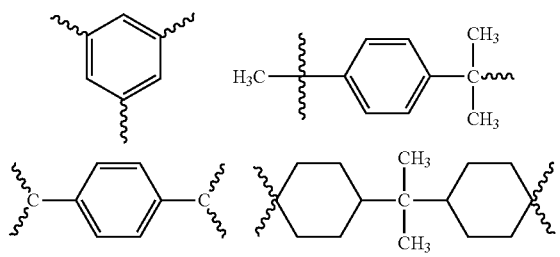

Herein the wavy line designates a valence bond.

In another aspect, the invention provides a method for preparing an aryl compound having glycidyl and (meth)allyl groups, represented by formula (1), comprising the step of reacting an aryl compound having (meth)allyl-containing phenol groups, represented by the general formula (2) with a 2-halomethyloxirane having the general formula (3).

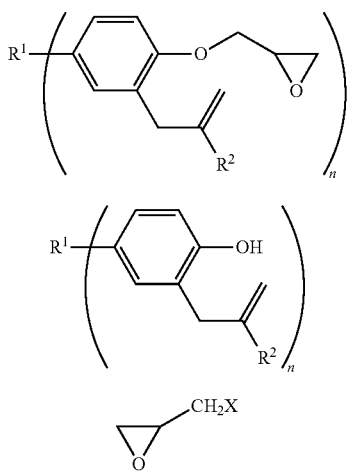

Herein $R^1$ is a tri- or tetravalent $C_3$-$C_{20}$ hydrocarbon group, $R^2$ is hydrogen or methyl, n is 3 or 4, and X is halogen.

ADVANTAGEOUS EFFECTS OF INVENTION

The aryl compound having at least three glycidyl groups and at least three (meth)allyl groups in the molecule is polymerizable in two ways using (meth)allyl groups and oxirane rings. Since the aryl compound has at least three functional groups of each type in the molecule, the resulting polymer has a three-dimensional crosslinked structure. A polymer as polymerized using such functional groups is further crosslinkable and curable, and the resulting polymer has satisfactory strength, heat resistance, weather resistance, and water resistance. Therefore, the aryl compound is useful as a macromonomer for heat resistant resin materials.

DESCRIPTION OF PREFERRED EMBODIMENTS

As used herein, the notation (Cn-Cm) means a group containing from n to m carbon atoms per group.

One embodiment of the invention is an aryl compound having at least three glycidyl groups and at least three (meth)allyl groups in the molecule, represented by the formula (1):

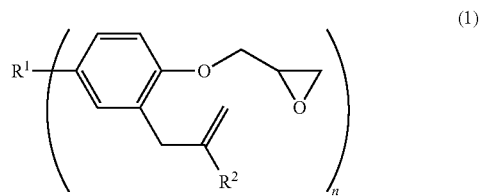

wherein $R^1$ is a trivalent or tetravalent $C_3$-$C_{20}$ hydrocarbon group, $R^2$ is hydrogen or methyl, and n is 3 or 4.

In formula (1), $R^1$ is a tri- or tetra-valent hydrocarbon group of 3 to 20 carbon atoms, preferably 3 to 15 carbon atoms. Specifically, $R^1$ is a substituted or unsubstituted tri- or tetravalent hydrocarbon group containing one or more, linear or branched aliphatic groups, alicyclic groups or aromatic groups. These linear or branched aliphatic groups, alicyclic groups, and aromatic groups may be contained alone or in combination of two or more.

Examples of the hydrocarbon group include n-propyl, isopropyl, n-butyl, isobutyl, t-butyl, pentyl, hexyl, cyclopentyl, cyclohexyl, bicyclohexyl, dicyclohexylmethyl, phenyl, tolyl, xylyl, benzyl, phenylethyl, phenylpropyl, methylbenzyl, and combinations thereof, with two or three hydrogen atoms being eliminated, which may be substituted or unsubstituted.

Preferably, $R^1$ is a tri- or tetravalent hydrocarbon group of at least 6 carbon atoms containing an aromatic group (aromatic ring) or alicyclic group (aliphatic ring), with the following groups being more preferred.

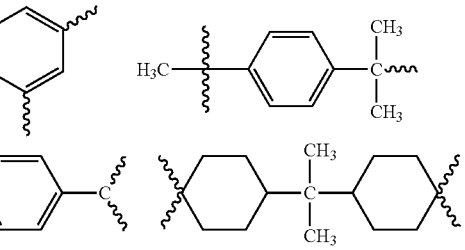

Herein the wavy line designates a valence bond.

Typical examples of the compound having formula (1) are shown below.

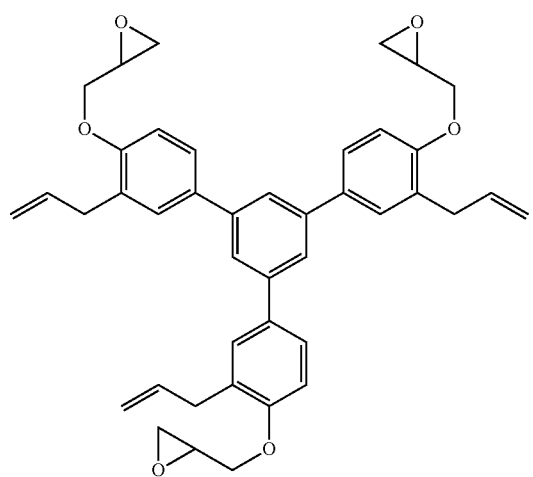
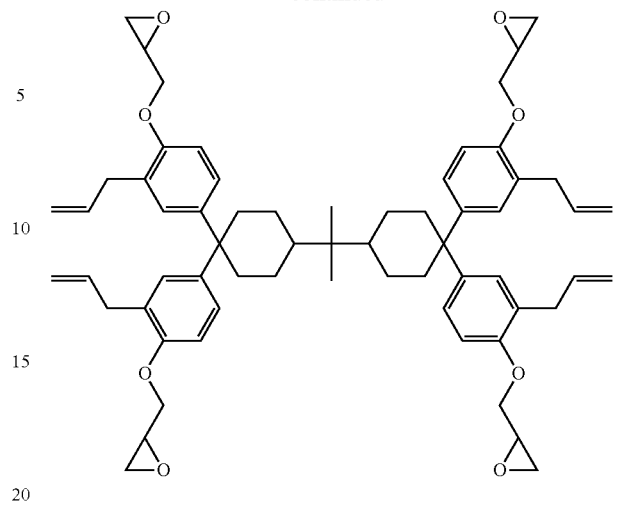
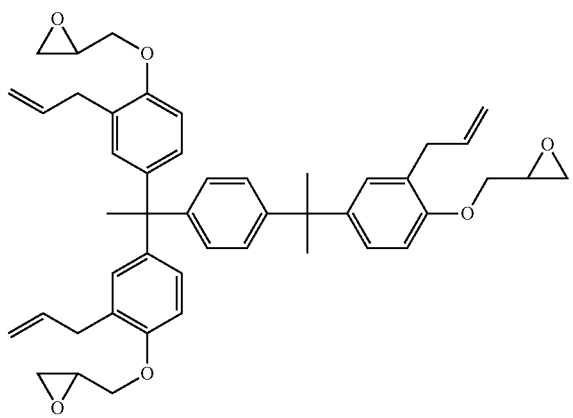
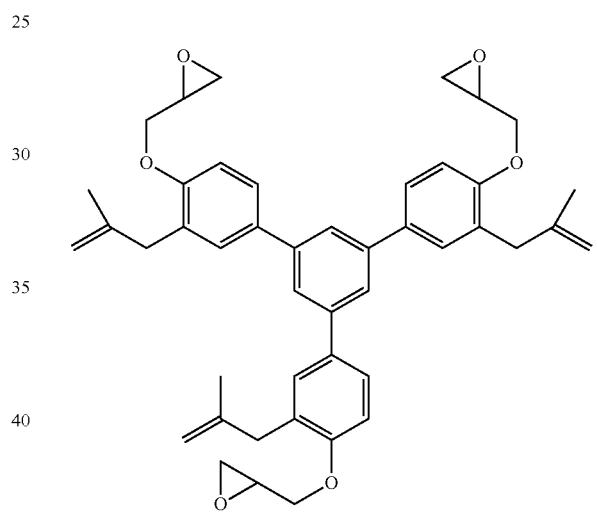
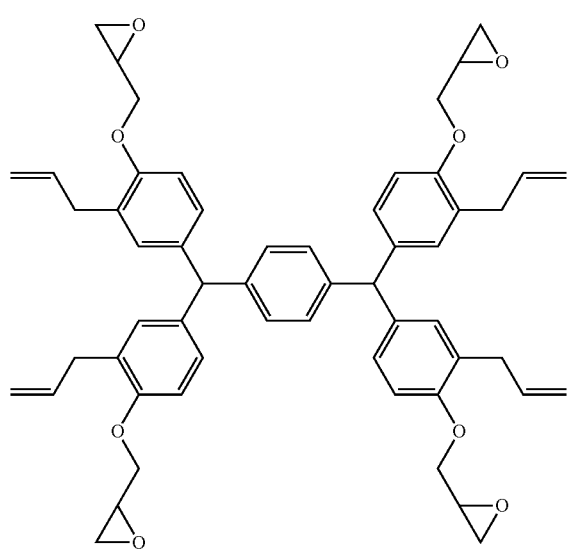
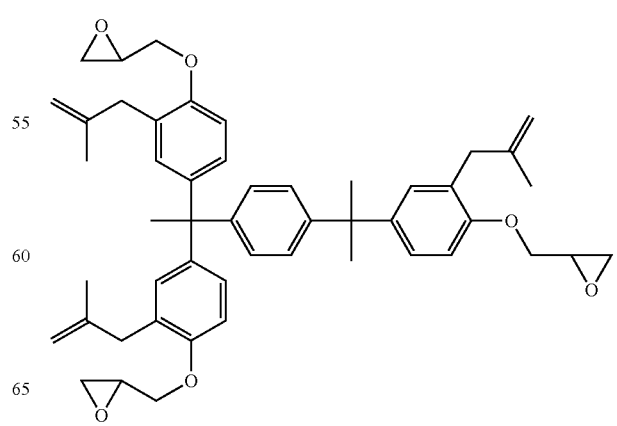

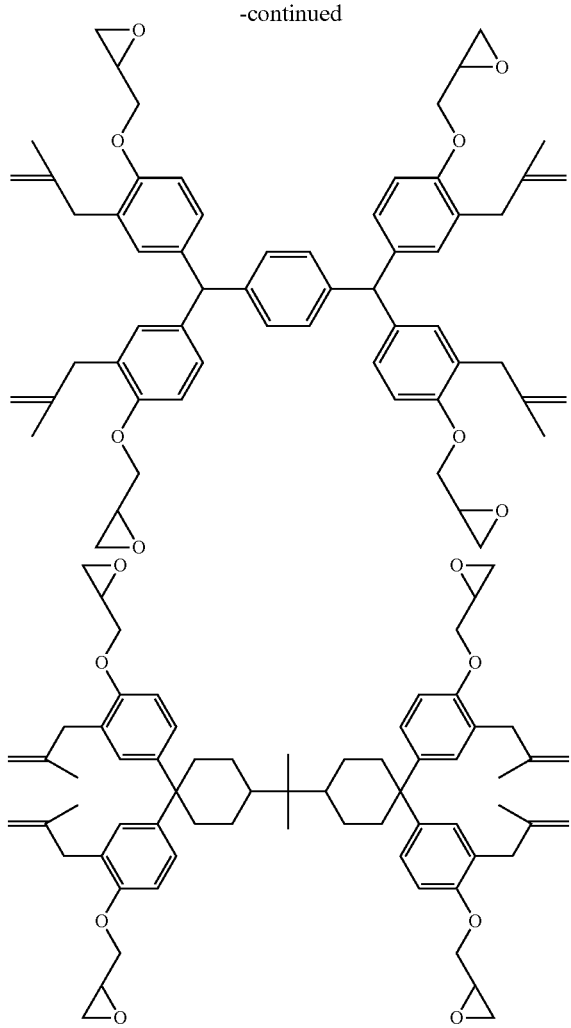

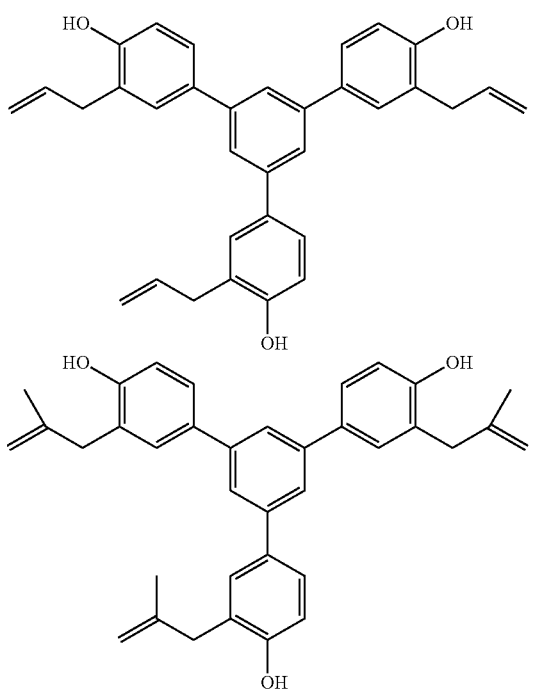

The aryl compound having formula (1) can be prepared by reacting an aryl compound having (meth)allyl-containing phenol groups, represented by the general formula (2):

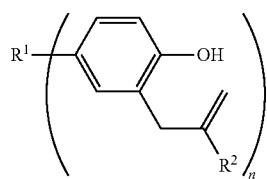

wherein $R^1$, $R^2$, and n are as defined above, with a 2-halomethyloxirane having the general formula (3):

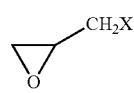

wherein X is a halogen atom, typically chlorine or bromine.

Typical examples of the aryl compound having (meth)allyl-containing phenol groups, represented by formula (2) are shown below.

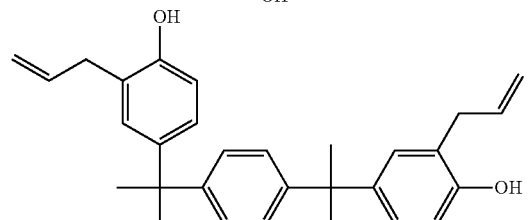

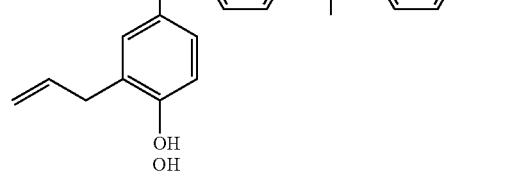

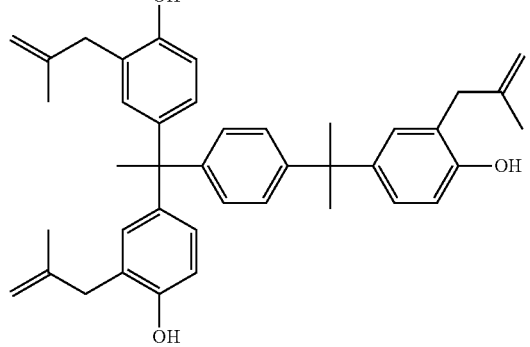

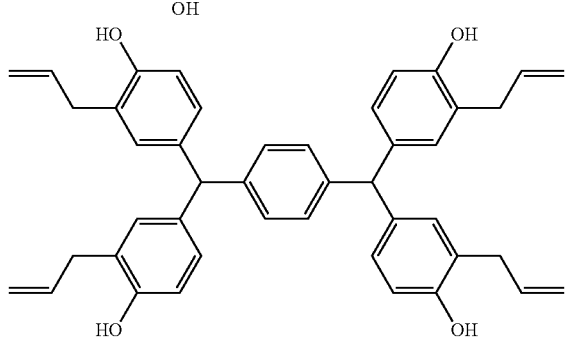

-continued

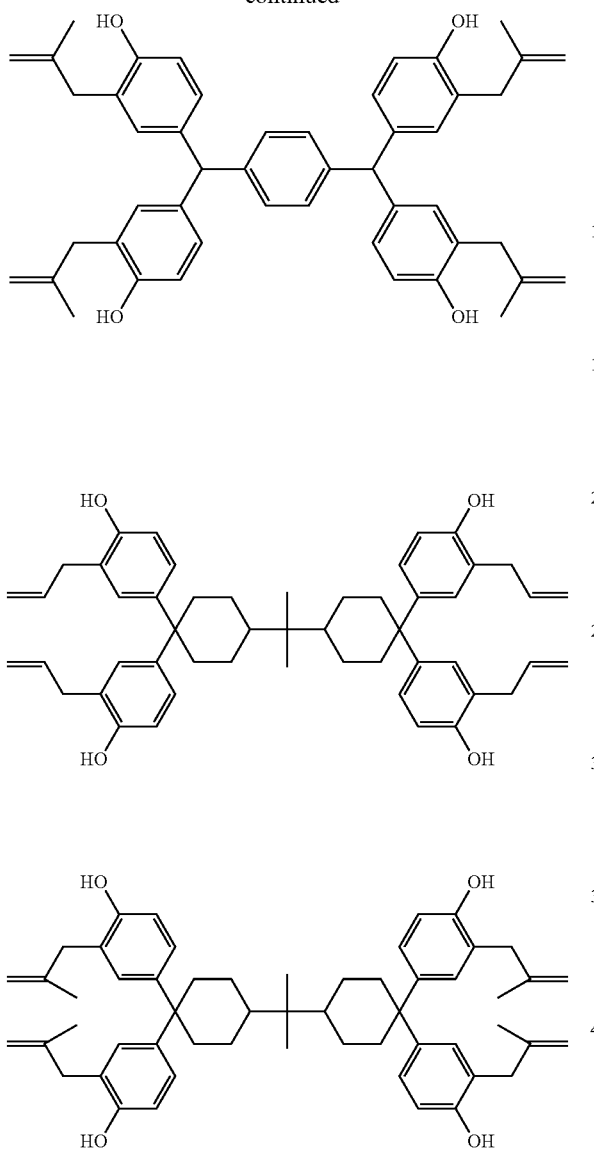

The compound of formula (2) is readily obtained by converting a well-known polyhydric phenol to a (meth)allyl ether and subjecting the ether to the known reaction of Claisen rearrangement. Typical examples of the polyhydric phenol are shown below.

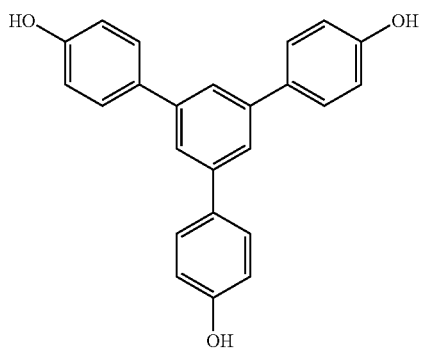

-continued

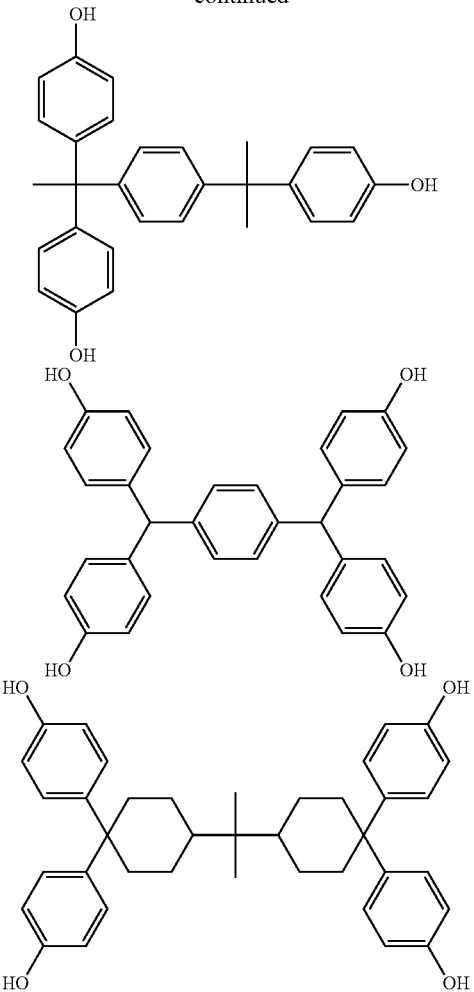

Typical of the 2-halomethyloxirane of formula (3) are 2-chloromethyloxirane and 2-bromomethyloxirane.

The compound of formula (2) may be reacted with the 2-halomethyloxirane of formula (3) in any desired ratio. Typically, the 2-halomethyloxirane of formula (3) is used in an amount of 1 to 10 moles, preferably 2 to 6 moles of halogen groups per mole of phenol groups on the compound of formula (2). Using the 2-halomethyloxirane of formula (3) in a large excess relative to the compound of formula (2), the compound of formula (1) is obtained. If the amount of 2-halomethyloxirane of formula (3) relative to the compound of formula (2) is reduced, an oxirane ring on the 2-halomethyloxirane of formula (3) may react with a phenol group on the compound of formula (2) to form a linked component, which does not adversely affect the invention.

In the reaction to form the compound of formula (1), a catalyst is optional. Typically, alkali metal hydroxides are used as the catalyst. Suitable alkali metal hydroxides include sodium hydroxide and potassium oxide. The alkali metal hydroxide may be added in solid form or as an aqueous solution or alcohol solution. The alkali metal hydroxide in solid form may be used alone or in admixture and added in divided portions or continuously to the reaction system. On use of an aqueous solution of the alkali metal hydroxide, which means that an excess of water is carried over from the aqueous solution to the reaction system, it is preferred to perform the reaction while removing water from the reaction system. The alkali metal hydroxide is preferably used in an amount of 1.0 to 1.2 equivalents, more preferably 1.0 to 1.1 equivalents per equivalent of phenolic hydroxyl group.

A solvent may be used in the reaction to form the compound of formula (1). If the 2-halomethyloxirane is added in a large excess, it may also serve as the reaction solvent. Optionally, a separate solvent may be added, and in that case, aprotic solvents are preferred. Examples of the aprotic solvent include dimethyl sulfone, dimethyl sulfoxide, dimethylformamide, 1,3-dimethyl-2-imidazolidinone, 1,4-dioxane, tetrahydrofuran, methyl ethyl ketone, methyl isobutyl ketone, toluene, xylene, benzene, pentane, hexane, heptane, octane, and decane. The aprotic solvent is typically used in an amount of 0 to 500% by weight, preferably 0 to 150% by weight based on the weight of 2-halomethyloxirane. When added, the amount of the solvent is preferably at least 5% by weight.

The reaction between the compound of formula (2) and 2-halomethyloxirane of formula (3) is performed at any desired temperature, typically in a range of 40° C. to 200° C., preferably 50° C. to 100° C. The reaction time is about 2 to about 30 hours, preferably 2 to 5 hours.

The reaction product as such or after washing with water is heated in vacuum to remove the excess 2-halomethyloxirane and the solvent, if used, or the like, obtaining the aryl compound of the invention. The aryl compound is preferably recovered by removing the by-product salt through filtration or water-washing at the end of reaction, and heating in vacuum to distill off the excess 2-halomethyloxirane, solvent and the like.

Since the aryl compound has at least three glycidyl groups and at least three (meth)allyl groups in the molecule, it may be polymerized by taking advantage of reactive (meth)allyl groups. Particularly, in the case of hydrosilylation reaction of the aryl compound with a SiH-containing siloxane compound, a high-molecular-weight silicone material having a glycidyl-containing three-dimensional crosslinked structure is obtained. In the case of reaction of the aryl compound with OH-containing silicone monomer units, phenol monomer units, or acrylic monomer units, reactive polymers are obtained.

When reactive epoxy is utilized, the aryl compound may be used as a curable material having a three-dimensional crosslinked structure. After polymerization using these groups, the remaining functional groups are still available for crosslinking and curing.

Therefore, the aryl compound is useful as a macromonomer for forming polymerizable heat resistant resin materials.

EXAMPLE

Examples of the invention are given below by way of illustration and not by way of limitation.

In Reference Examples, the weight average molecular weight (Mw) of a polymer is measured by gel permeation chromatography (GPC) versus monodisperse polystyrene standards using GPC columns TSKgel Super HZM-H (Tosoh Corp.) under analytical conditions: flow rate 0.6 mL/min, tetrahydrofuran as the elute, and column temperature 40° C. All parts are by weight (pbw). The abbreviation NMR stands for nuclear magnetic resonance.

Example 1

In a 1-L separable flask equipped with a nitrogen gas inlet tube, thermometer, Dimroth condenser, vacuum controller, and aspirator, 109 g (0.2 mol) of the allyl-containing compound of the following formula was dissolved in 100 g of toluene and 167 g (1.8 mol) of 2-chloromethyloxirane.

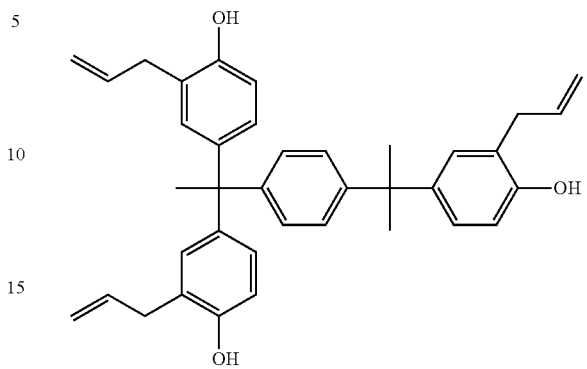

To the solution, 26.4 g (0.66 mol) of KOH was gradually added. The contents were heated at 60° C. and allowed to react for 3 hours. At the end of reaction, 300 g of pure water was added to the reaction solution to dissolve the precipitated salt whereupon the reaction solution separated into an organic layer and a water layer. The organic layer was 332 g and the water layer was 369 g. From the organic layer, 2-chloromethyloxirane and toluene were distilled off in vacuum, yielding 135 g of a yellowish brown solid compound. On epoxy equivalent measurement and $^1$H-NMR spectroscopy, the resulting compound was identified to be aryl compound A having three allyl groups and three glycidyl groups in the molecule, represented by the following formula. The $^1$H-NMR data are shown in Table 1.

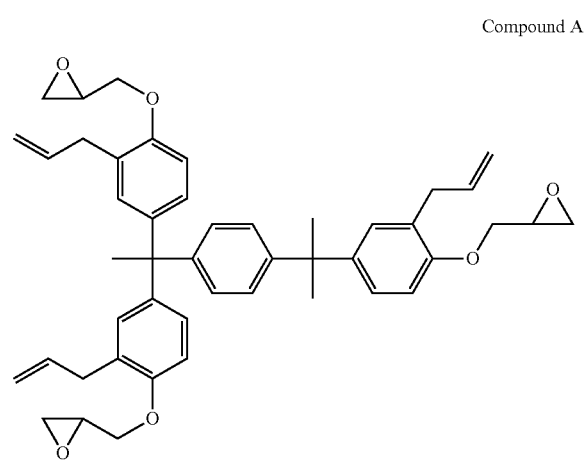 [SMILES: C=CCc1cc(C(C)(C)c2ccc(C(C)(c3ccc(OCC4CO4)c(CC=C)c3)c3ccc(OCC4CO4)c(CC=C)c3)cc2)ccc1OCC1CO1]

Compound A

TABLE 1

| Peak | δ, ppm | |
|---|---|---|
| j, j' | 1.64 | 6 H |
| m | 2.18 | 3 H |
| a, s, s' | 2.64 to 2.77 | 6 H |
| b, r, r', g, t, t' | 3.36 to 3.41 | 9 H |
| c, q, q' | 3.86 to 4.11 | 6 H |
| i, v, v' | 5.05 to 5.10 | 6 H |
| h, u, u' | 5.99 to 6.08 | 3 H |
| d, e, f, k, k', l, l', n, n', o, o', p, p' | 6.66 to 7.14 | 13 H |

TABLE 1-continued

| Peak | δ, ppm |
|------|--------|

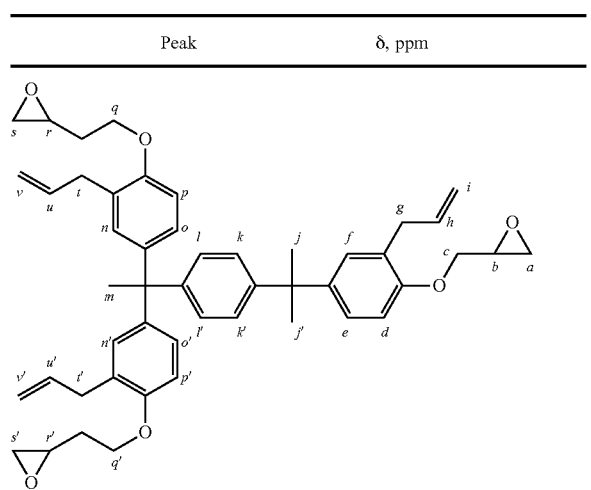

Example 2

In a 1-L separable flask equipped with a nitrogen gas inlet tube, thermometer, Dimroth condenser, dropping funnel, vacuum controller, and aspirator, 127 g (0.2 mol) of the allyl-containing compound of the following formula was dissolved in 100 g of toluene and 167 g (1.8 mol) of 2-chloromethyloxirane.

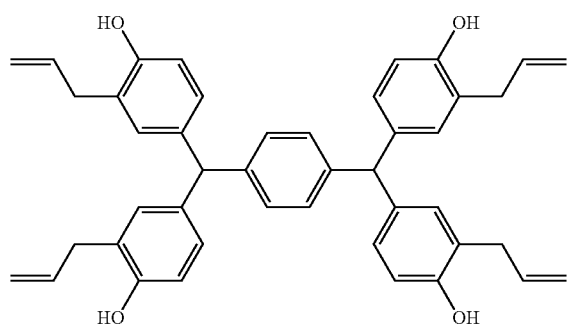 [SMILES: C=CCc1cc(C(c2ccc(C(c3ccc(O)c(CC=C)c3)c3ccc(O)c(CC=C)c3)cc2)c2ccc(O)c(CC=C)c2)ccc1O]

To the solution, 132 g of 20 wt % KOH methanol solution (0.66 mol of KOH) was slowly added dropwise. The contents were heated at 60° C. and allowed to react for 3 hours. At the end of reaction, 300 g of pure water was added to the reaction solution to dissolve the precipitated salt whereupon the reaction solution separated into an organic layer and a water layer. The organic layer was 442 g and the water layer was 382 g. From the organic layer, 2-chloromethyloxirane and the solvent were distilled off in vacuum, yielding 155 g of a brown solid compound. On epoxy equivalent measurement and $^1$H-NMR spectroscopy, the resulting compound was identified to be aryl compound B having four allyl groups and four glycidyl groups in the molecule, represented by the following formula.

Compound B

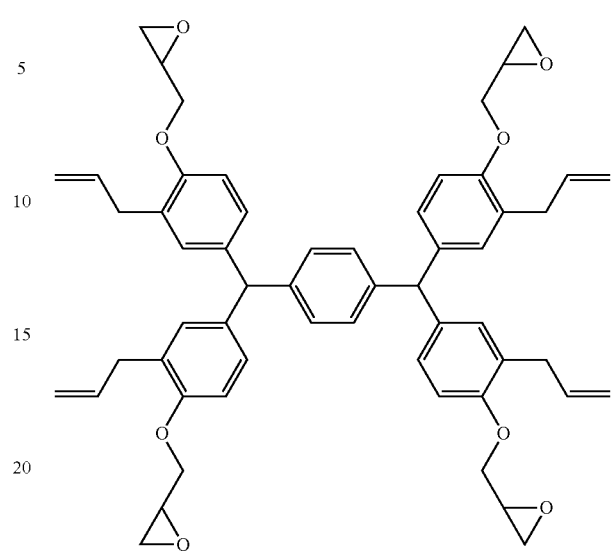

Example 3

In a 1-L separable flask equipped with a nitrogen gas inlet tube, thermometer, Dimroth condenser, dropping funnel, vacuum controller, and aspirator, 147 g (0.2 mol) of the allyl-containing compound of the following formula was dissolved in 100 g of toluene and 167 g (1.8 mol) of 2-chloromethyloxirane.

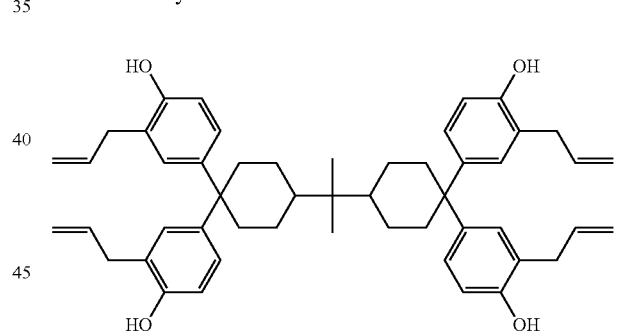

To the solution, 132 g of 20 wt % KOH methanol solution (0.66 mol of KOH) was slowly added dropwise. The contents were heated at 60° C. and allowed to react for 3 hours. At the end of reaction, 300 g of pure water was added to the reaction solution to dissolve the precipitated salt whereupon the reaction solution separated into an organic layer and a water layer. The organic layer was 420 g and the water layer was 384 g. From the organic layer, 2-chloromethyloxirane and the solvent were distilled off in vacuum, yielding 175 g of a brown solid compound. On epoxy equivalent measurement and $^1$H-NMR spectroscopy, the resulting compound was identified to be aryl compound C having four allyl groups and four glycidyl groups in the molecule, represented by the following formula.

Compound C

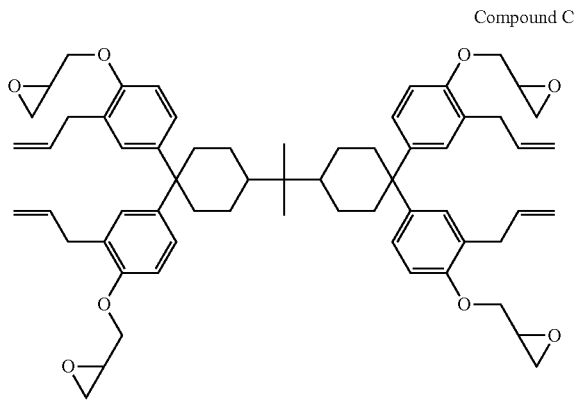 [SMILES: C=CCc1cc(C2(c3ccc(OCC4CO4)c(CC=C)c3)CCC(C(C)(C)C3CCC(c4ccc(OCC5CO5)c(CC=C)c4)(c4ccc(OCC5CO5)c(CC=C)c4)CC3)CC2)ccc1OCC1CO1]

Compound D

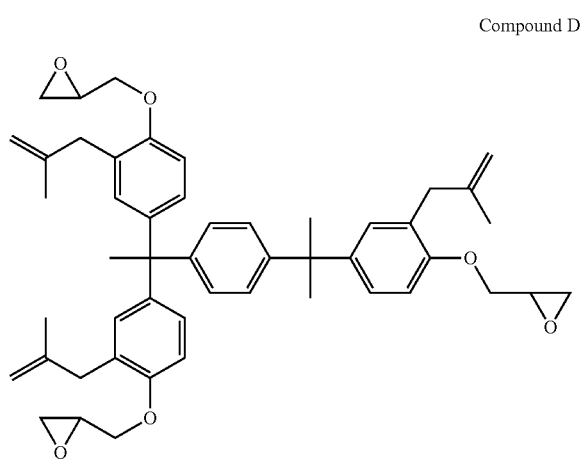

Example 4

The same reaction and post-treatment procedure of Example 1 was repeated except that the allyl-containing compound of the following formula:

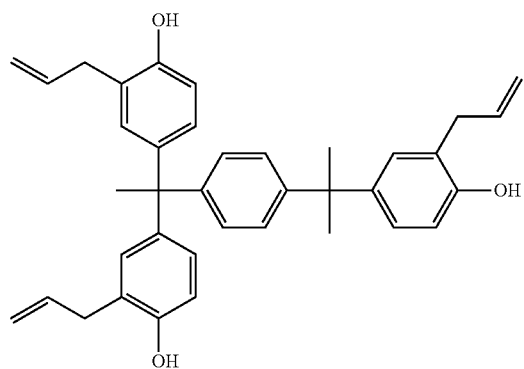 [SMILES: C=CCc1cc(C(C)(C)c2ccc(C(C)(c3ccc(O)c(CC=C)c3)c3ccc(O)c(CC=C)c3)cc2)ccc1O]

was replaced by 117 g (0.2 mol) of the methallyl-containing compound of the following formula.

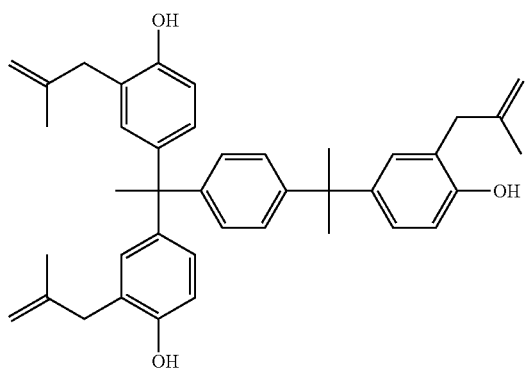 [SMILES: C=C(C)Cc1cc(C(C)(C)c2ccc(C(C)(c3ccc(O)c(CC(=C)C)c3)c3ccc(O)c(CC(=C)C)c3)cc2)ccc1O]

There was obtained 135 g of a brown solid compound. On infrared absorption spectroscopy and $^1$H-NMR spectroscopy, the resulting compound was identified to be aryl compound D having three methallyl groups and three glycidyl groups in the molecule, represented by the following formula.

Comparative Example 1

In a 1-L separable flask equipped with a nitrogen gas inlet tube, thermometer, Dimroth condenser, vacuum controller, and aspirator, 83 g (0.2 mol) of the allyl-containing compound of the following formula was dissolved in 100 g of toluene and 167 g (1.8 mol) of 2-chloromethyloxirane.

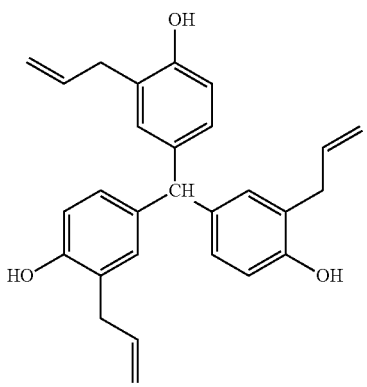 [SMILES: C=CCc1cc(C(c2ccc(O)c(CC=C)c2)c2ccc(O)c(CC=C)c2)ccc1O]

To the solution, 26.4 g (0.66 mol) of KOH was gradually added. The contents were heated at 60° C. and allowed to react for 3 hours. At the end of reaction, 300 g of pure water was added to the reaction solution to dissolve the precipitated salt whereupon the reaction solution separated into an organic layer and a water layer. The organic layer was 332 g and the water layer was 369 g. From the organic layer, 2-chloromethyloxirane and toluene were distilled off in vacuum, yielding 98 g of a yellowish brown solid compound. On epoxy equivalent measurement and $^1$H-NMR spectroscopy, the resulting compound was identified to be aryl compound E having three allyl groups and three glycidyl groups in the molecule, represented by the following formula.

Compound E

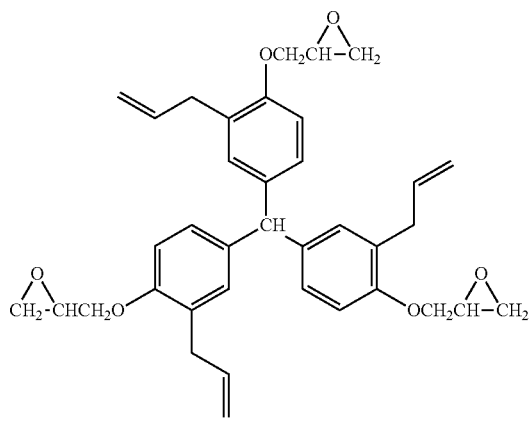

The compounds used in Reference Examples and Comparative Reference Examples are shown below.

i-1: Compound A obtained in Example 1

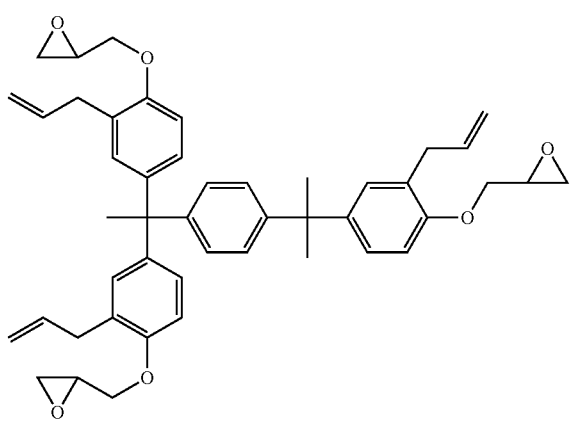 [SMILES: C=CCc1cc(C(C)(C)c2ccc(C(C)(c3ccc(OCC4CO4)c(CC=C)c3)c3ccc(OCC4CO4)c(CC=C)c3)cc2)ccc1OCC1CO1]

i-2: available from Shin-Etsu Chemical Co., Ltd.

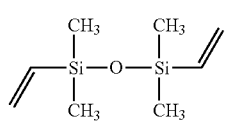

i-3: available from Shin-Etsu Chemical Co., Ltd.

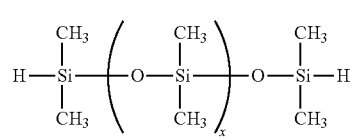

i-4: available from Shin-Etsu Chemical Co., Ltd.

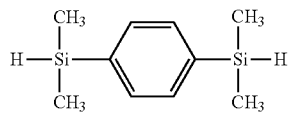

i-5: Compound B obtained in Example 2

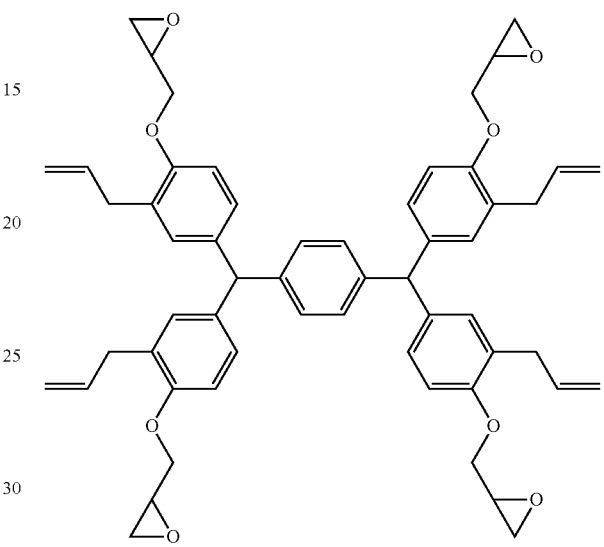

i-6: Compound E obtained in Comparative Example 1

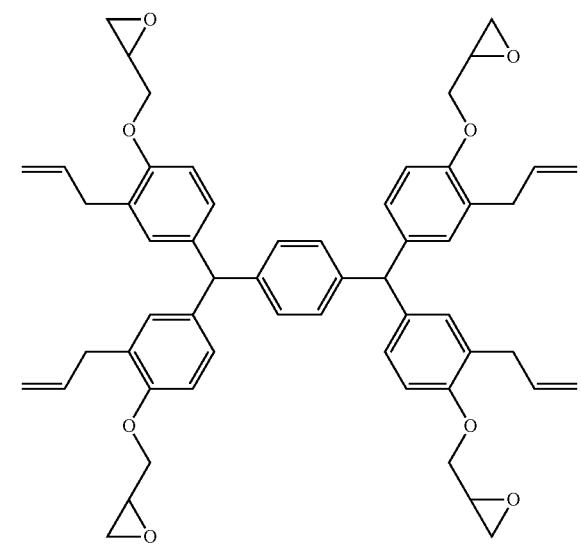 [SMILES: C=CCc1cc(C(c2ccc(C(c3ccc(OCC4CO4)c(CC=C)c3)c3ccc(OCC4CO4)c(CC=C)c3)cc2)c2ccc(OCC3CO3)c(CC=C)c2)ccc1OCC1CO1]

RE-810NM: available from Nippon Kayaku Co., Ltd.

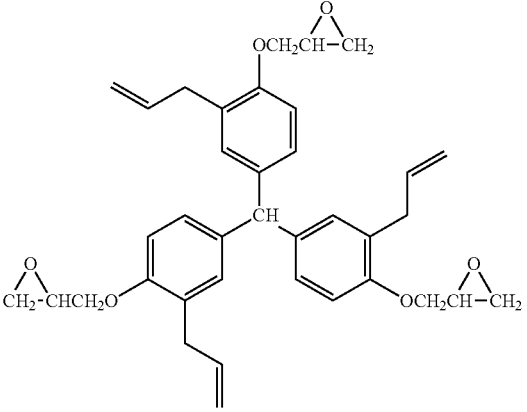

Reference Example 1

A 2-L separable flask equipped with a nitrogen gas inlet tube, thermometer, Dimroth condenser, vacuum controller, and aspirator was charged with 11.9 g (0.017 mol) of the compound having formula (i-1) (i.e., Compound A in Example 1), 14 g (0.075 mol) of the compound having formula (i-2) and 63.1 g (0.15 mol) of RE-810NM, then with 1,000 g of toluene, and heated at 70° C. Thereafter, 0.25 g of a toluene solution of chloroplatinic acid (platinum concentration 0.5 wt %) was added and 154.7 g (0.05 mol) of the compound having formula (i-3) wherein x=40 and 38.9 g (0.2 mol) of the compound having formula (i-4) were added dropwise over 1 hour. The total moles of hydrosilyl groups to the total moles of alkenyl groups was 1/1. At the end of dropwise addition, the reaction solution was heated at 100° C. and aged for 6 hours. Toluene was distilled off in vacuum from the reaction solution, yielding a resin (I) having Mw of 45,000.

Reference Example 2

Polymer of Compound B

A 2-L separable flask equipped with a nitrogen gas inlet tube, thermometer, Dimroth condenser, vacuum controller, and aspirator was charged with 10.7 g (0.013 mol) of the compound having formula (i-5) (i.e., Compound B in Example 2), 14 g (0.075 mol) of the compound having formula (i-2) and 63.1 g (0.15 mol) of RE-810NM, then with 1,000 g of toluene, and heated at 70° C. Thereafter, 0.25 g of a toluene solution of chloroplatinic acid (platinum concentration 0.5 wt %) was added and 154.7 g (0.05 mol) of the compound having formula (i-3) wherein x=40 and 38.9 g (0.2 mol) of the compound having formula (i-4) were added dropwise over 1 hour. The total moles of hydrosilyl groups to the total moles of alkenyl groups was 1/1. At the end of dropwise addition, the reaction solution was heated at 100° C. and aged for 5 hours. Toluene was distilled off in vacuum from the reaction solution, yielding a resin (II) having Mw of 42,000.

Comparative Reference Example 1

A 2-L separable flask equipped with a nitrogen gas inlet tube, thermometer, Dimroth condenser, vacuum controller, and aspirator was charged with 9.9 g (0.017 mol) of the compound having formula (i-6) (i.e., Compound E in Comparative Example 1) and 14 g (0.075 mol) of the compound having formula (i-2), then with 1,000 g of toluene, and heated at 70° C. Thereafter, 0.25 g of a toluene solution of chloroplatinic acid (platinum concentration 0.5 wt %) was added and 154.7 g (0.05 mol) of the compound having formula (i-3) wherein x=40 and 38.9 g (0.2 mol) of the compound having formula (i-4) were added dropwise over 1 hour. The total moles of hydrosilyl groups to the total moles of alkenyl groups was 1/1. At the end of dropwise addition, the reaction solution was heated at 100° C. and aged for 6 hours. Toluene was distilled off in vacuum from the reaction solution, yielding a resin (III) having Mw of 35,000.

Reference Examples 3 and 4 and Comparative Reference Example 2

Curable compositions were prepared by mixing an epoxy-modified silicone resin (resins (I) to (III) obtained in Reference Examples 1 and 2 and Comparative Reference Example 1), a crosslinker (CL) having the following structural formula, and a solvent in accordance with the formulation (type and pbw) shown in Table 2.

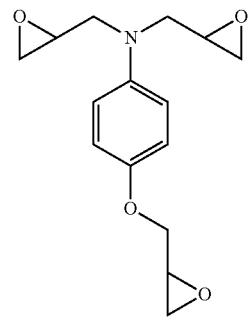

Crosslinker (CL)

TABLE 2

|  | Resin | pbw | Crosslinker | pbw | Solvent | pbw |
| --- | --- | --- | --- | --- | --- | --- |
| Reference Example 3 | (I) | 100 | CL | 15 | cyclopentanone | 100 |
| Reference Example 4 | (II) | 100 |  |  |  |  |
| Comparative Reference Example 2 | (III) | 100 |  |  |  |  |

The curable compositions obtained in Reference Examples were evaluated for outer appearance, heat resistance, adhesion, and solvent resistance by the following tests. The results are shown in Table 3.

Outer Appearance

The curable composition solution was spin coated onto a silicon substrate, then baked on a hot plate at 130° C. for 2 minutes and further at 190° C. for 1 hour, forming a cured film of 30 μm thick. The cured film was inspected for outer appearance by visual observation and tack by finger touch. The film was rated good "○" when neither cracks nor tack was found and poor "×" when cracks and tack were found.

Heat Resistance Test

The curable composition solution was spin coated onto a silicon substrate, then baked on a hot plate at 130° C. for 2 minutes and further at 190° C. for 1 hour, forming a cured film of 30 μm thick. The cured film was placed in a nitrogen atmosphere oven at 250° C. for 2 hours and then heated on a hot plate at 270° C. for 10 minutes. The outer appearance of the film was observed for anomaly. The film was rated good "○" when appearance anomalies such as voids and peels were not found and poor "×" when appearance anomalies were found.

Adhesion Test

The curable composition solution was spin coated onto a silicon substrate or copper-deposited silicon substrate, then baked at 130° C. for 2 minutes and further at 190° C. for 1 hour, forming a cured film. The cured film was placed in a nitrogen atmosphere oven at 250° C. for 2 hours and then heated on a hot plate at 270° C. for 10 minutes. The film was evaluated for adhesion after temperature exposure by the cross-cut peeling test of JIS K5400 at room temperature. In Table 3, the fractional number represents the number of unpeeled sections per 100 cross-cut sections. Specifically, 100/100 means that all sections are kept intact or unpeeled, and 0/100 means that all sections are peeled off.

Solvent Resistance Test

The curable composition solution was spin coated onto a 6-inch (150 mm diameter) silicon wafer, forming a coating of 30 μm thick. The coating was heat dried at 150° C. for 2 minutes and then at 200° C. for 2 minutes, after which it was immersed in N-methylpyrrolidone (NMP) at 25° C. for 10 minutes. The coating was visually inspected whether or not it was dissolved away. The coating was rated good "○" when coating dissolution was not observed and poor "×" when coating dissolution was observed.

TABLE 3

|  |  | Reference Example 3 | Reference Example 4 | Comparative Reference Example 2 |
|---|---|---|---|---|
| Outer appearance |  | ○ | ○ | ○ |
| Heat resistance |  | ○ | ○ | X |
| Adhesion (cross-cut peeling test) | Silicon | 100/100 | 100/100 | 90/100 |
|  | Cu-deposited silicon | 100/100 | 100/100 | 70/100 |
| Solvent resistance |  | ○ | ○ | ○ |

It has been demonstrated that the novel aryl compound having at least three glycidyl groups and at least three (meth)allyl groups in the molecule is useful as a macromonomer for heat resistant resin materials.

It is noted that the invention is not limited to the aforementioned embodiments. While the embodiments are merely exemplary, any embodiments having substantially the same construction as the technical concept set forth in the following claims and exerting equivalent functions and results are believed to be within the spirit and scope of the invention.

Japanese Patent Application No. 2016-001905 is incorporated herein by reference.

Although some preferred embodiments have been described, many modifications and variations may be made thereto in light of the above teachings. It is therefore to be understood that the invention may be practiced otherwise than as specifically described without departing from the scope of the appended claims.

The invention claimed is:

1. An aryl compound terminated with glycidyl and (meth)allyl groups, having the general formula (1):

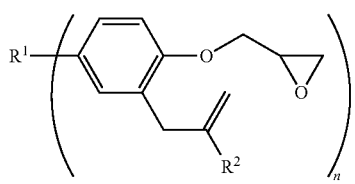

(1)

wherein $R^1$ is a trivalent or tetravalent $C_3$-$C_{20}$ hydrocarbon group, $R^2$ is hydrogen or methyl, and n is 3 or 4.

2. The aryl compound of claim 1 wherein $R^1$ in formula (1) is a trivalent or tetravalent $C_3$-$C_{15}$ hydrocarbon group.

3. The aryl compound of claim 2 wherein $R^1$ has at least an aromatic or alicyclic group.

4. The aryl compound of claim 3 wherein $R^1$ is selected from the following groups:

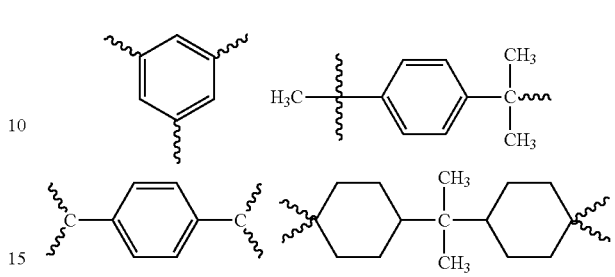

wherein the wavy line designates a valence bond.

5. A method for preparing an aryl compound having glycidyl and (meth)allyl groups, represented by the general formula (1):

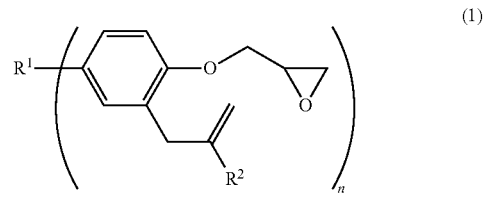

(1)

wherein $R^1$ is a trivalent or tetravalent $C_3$-$C_{20}$ hydrocarbon group, $R^2$ is hydrogen or methyl, and n is 3 or 4, the method comprising the step of reacting an aryl compound having (meth)allyl-containing phenol groups, represented by the general formula (2):

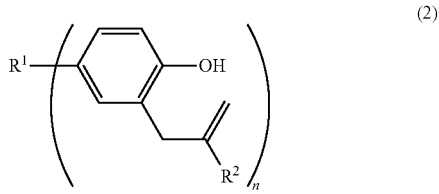

(2)

wherein $R^1$ is a trivalent or tetravalent $C_3$-$C_{20}$ hydrocarbon group, $R^2$ is hydrogen or methyl, and n is 3 or 4, with a 2-halomethyloxirane having the general formula (3):

(3)

wherein X is halogen.

* * * * *